(12) United States Patent
Augarten

(10) Patent No.: US 9,265,422 B2
(45) Date of Patent: Feb. 23, 2016

(54) SYSTEM AND METHOD FOR DETERMINING AN ADJUSTMENT TO A GASTRIC BAND BASED ON SATIETY STATE DATA AND WEIGHT LOSS DATA

(75) Inventor: Mike Augarten, Goleta, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 1027 days.

(21) Appl. No.: 12/768,496

(22) Filed: Apr. 27, 2010

(65) Prior Publication Data

US 2011/0263929 A1    Oct. 27, 2011

(51) Int. Cl.
*A61F 5/00* (2006.01)
*A61B 5/00* (2006.01)
*A61B 5/07* (2006.01)
*A61N 1/372* (2006.01)

(52) U.S. Cl.
CPC .............. *A61B 5/0031* (2013.01); *A61F 5/0059* (2013.01); *A61B 5/073* (2013.01); *A61F 2005/002* (2013.01); *A61F 2005/0023* (2013.01); *A61N 1/37247* (2013.01)

(58) Field of Classification Search
CPC ...................... A61B 5/03; A61B 5/076; A61B 2017/00818; A61F 5/0003; A61F 5/005; A61F 5/0053; A61F 5/0056; A61F 5/0059; A61F 2/0004; A61F 2/004
USPC .................. 600/29–32, 37; 604/909; 606/157
See application file for complete search history.

(56) References Cited

U.S. PATENT DOCUMENTS

| | | | |
|---|---|---|---|
| 4,592,339 A | 6/1986 | Kuzmak |
| 4,696,288 A | 9/1987 | Kuzmak |
| 4,883,467 A | 11/1989 | Franetzki |
| 5,120,313 A | 6/1992 | Elftman |
| 5,259,399 A | 11/1993 | Brown |
| 5,360,445 A | 11/1994 | Goldowsky |
| 5,535,752 A | 7/1996 | Halperin |
| 5,554,113 A | 9/1996 | Novak |
| 5,562,714 A | 10/1996 | Grevious |
| 5,676,162 A | 10/1997 | Larson, Jr. |
| 5,766,232 A | 6/1998 | Grevious |
| 6,024,704 A | 2/2000 | Meador |
| 6,221,024 B1 | 4/2001 | Miesel |
| 6,417,750 B1 | 7/2002 | Sohn |
| 6,470,892 B1 | 10/2002 | Forsell |
| 6,754,527 B2 | 6/2004 | Stroebel |

(Continued)

FOREIGN PATENT DOCUMENTS

WO    WO 2006/102626    9/2006

*Primary Examiner* — Charles A Marmor, II
*Assistant Examiner* — Carrie R Dorna
(74) *Attorney, Agent, or Firm* — Gordon & Jacobson, P.C.

(57) ABSTRACT

A system and method for determining an adjustment to a gastric band, and more specifically to determining an adjustment to a gastric band based on satiety state data and weight loss data. The gastric band information system can determine an adjustment of the gastric band using a gastric band adjustment algorithm. The gastric band information system can wirelessly transmit the adjustment to the gastric band. The gastric band information system can receive gastric band data, weight data, glucose data, and/or blood pressure data and display a gastric band chart, a weight chart, and/or a blood pressure chart. The gastric band information system can also receive gastric band implantation data, patient data, and/or any other medical data. The various data can be received from a computer or medical devices in a wired or wireless manner.

20 Claims, 19 Drawing Sheets

(56) References Cited

U.S. PATENT DOCUMENTS

| | | |
|---|---|---|
| 6,804,558 B2 | 10/2004 | Haller |
| 6,834,201 B2 | 12/2004 | Gillies |
| 6,871,090 B1 | 3/2005 | He |
| 6,940,467 B2 | 9/2005 | Fischer |
| 7,021,147 B1 | 4/2006 | Subramanian |
| 7,058,434 B2 | 6/2006 | Wang |
| 7,191,007 B2 | 3/2007 | Desai |
| 7,283,867 B2 | 10/2007 | Strother |
| 7,311,716 B2 | 12/2007 | Byrum |
| 7,351,198 B2 | 4/2008 | Byrum |
| 7,351,240 B2 | 4/2008 | Hassler |
| 7,367,340 B2 | 5/2008 | Nelson |
| 7,367,937 B2 | 5/2008 | Jambor |
| 7,374,565 B2 | 5/2008 | Hassler, Jr. |
| 7,390,294 B2 | 6/2008 | Hassler |
| 7,396,353 B2 | 7/2008 | Lorenzen |
| 7,481,763 B2 | 1/2009 | Hassler |
| 7,500,944 B2 | 3/2009 | Byrum |
| 7,584,002 B2 | 9/2009 | Burnes |
| 7,594,885 B2 | 9/2009 | Byrum |
| 7,599,743 B2 | 10/2009 | Hassler |
| 7,599,744 B2 | 10/2009 | Giordano |
| 7,615,001 B2 | 11/2009 | Jambor |
| 7,618,365 B2 | 11/2009 | Jambor |
| 7,658,196 B2 | 2/2010 | Ferreri |
| 7,699,770 B2 | 4/2010 | Hassler |
| 2001/0011543 A1 | 8/2001 | Forsell |
| 2004/0267288 A1 | 12/2004 | Byrum |
| 2004/0267292 A1 | 12/2004 | Byrum |
| 2005/0002984 A1 | 1/2005 | Byrum |
| 2005/0070937 A1 | 3/2005 | Jambor |
| 2005/0240155 A1 | 10/2005 | Conlon |
| 2005/0288739 A1 | 12/2005 | Hassler |
| 2005/0288740 A1 | 12/2005 | Hassler |
| 2006/0173238 A1 | 8/2006 | Starkebaum |
| 2006/0189887 A1 | 8/2006 | Hassler |
| 2006/0189888 A1 | 8/2006 | Hassler |
| 2006/0199997 A1 | 9/2006 | Hassler |
| 2006/0211912 A1 | 9/2006 | Dlugos |
| 2006/0211913 A1 | 9/2006 | Hassler |
| 2006/0235448 A1 | 10/2006 | Roslin |
| 2006/0247722 A1 | 11/2006 | Maschino et al. |
| 2007/0015954 A1 | 1/2007 | Dlugos |
| 2007/0015955 A1 | 1/2007 | Tsonton |
| 2007/0156013 A1 | 7/2007 | Birk |
| 2007/0232848 A1 | 10/2007 | Forsell |
| 2007/0235083 A1 | 10/2007 | Dlugos |
| 2007/0250086 A1 | 10/2007 | Wiley |
| 2008/0009680 A1 | 1/2008 | Hassler |
| 2008/0015406 A1 | 1/2008 | Dlugos |
| 2008/0221598 A1 | 9/2008 | Dlugos |
| 2008/0249806 A1 | 10/2008 | Dlugos |
| 2008/0250340 A1 | 10/2008 | Dlugos |
| 2008/0250341 A1 | 10/2008 | Dlugos |
| 2009/0157106 A1 | 6/2009 | Marcotte |
| 2009/0171378 A1 | 7/2009 | Coe |
| 2009/0192404 A1 | 7/2009 | Ortiz |
| 2009/0192533 A1 | 7/2009 | Dlugos, Jr. et al. |
| 2009/0192541 A1 | 7/2009 | Ortiz et al. |
| 2009/0204131 A1 | 8/2009 | Ortiz |
| 2009/0204132 A1 | 8/2009 | Ortiz |
| 2009/0222065 A1 | 9/2009 | Dlugos, Jr. et al. |
| 2010/0010291 A1 | 1/2010 | Birk |

SYSTEM AND METHOD FOR DETERMINING AN ADJUSTMENT TO A GASTRIC BAND BASED ON SATIETY STATE DATA AND WEIGHT LOSS DATA

FIELD

The present invention generally relates to a system and method for determining an adjustment to a gastric band, and more specifically to determining an adjustment to a gastric band based on satiety state data and weight loss data.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the passage of food into a lower portion of the stomach. When the stoma is of an appropriate size that is restricted by a gastric band, food held in the upper portion of the stomach provides a feeling of satiety or fullness that discourages overeating. Unlike gastric bypass procedures, the gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

However, adjustment of the gastric band may be dependent on several pieces of data. Such data are conventionally collected as hand written documents, or typed data entry into computer spreadsheets or forms. In general, the methods used to collect gastric band related information have several disadvantages including minimal automation, lack of strong influence for consistency of format and content from one office to the next, and various degrees of difficulty in protecting and retrieving the information.

Some data collection systems have also been disclosed, but these devices have certain disadvantages. For example, Burnes, U.S. Pat. No. 7,584,002, generally discloses aggregation from external data sources within an implantable medical device, but Burnes collects data at an implanted device.

Strother, U.S. Pat. No. 7,283,867, discloses an implantable system and method for acquisition and processing of electrical signals from muscles and/or nerves and/or central nervous system tissue. However, Strother is not directed to adjustment of gastric bands.

Thus, there is a need for a method and system for displaying gastric band information, and more specifically to gastric band information which can support adjustment of a gastric band.

SUMMARY

Generally described herein is a band information system which can determine an adjustment to a gastric band based on satiety state data and weight loss data. The band information system can also be used to display gastric band information, medical data and/or patient data which can also be used to display various medical charts. In one embodiment, the band information system determines an optimal amount of band constriction (i.e., how much saline to inject or to withdraw from the gastric band) at various times (e.g., when sleeping, when eating, when upright, when nauseous, when weight loss is too low or too high, etc.) based upon the satiety state data, the weight loss data, the medical data and/or the patient data.

In one embodiment, the present invention is a portable gastric band information system including a memory unit, a display unit, and a micro controller connected to the memory unit and the display unit, the micro controller configured to determine an adjustment of a gastric band for a patient, receive gastric band pressure data for the gastric band, display a gastric band pressure chart on the display unit based on the gastric band pressure data, receive weight data for the patient, and display a weight chart on the display unit based on the weight data.

In another embodiment, the present invention is a portable gastric band information system including a memory unit, a display unit, and a micro controller connected to the memory unit and the display unit, the micro controller configured to determine an adjustment of a gastric band for a patient, receive gastric band pressure data for the gastric band, display a gastric band pressure chart on the display unit based on the gastric band pressure data, receive glucose data for the patient, and display a glucose chart on the display unit based on the glucose data.

In another embodiment, the present invention is a portable gastric band information system including a memory unit, a display unit, a wireless connection unit, and a micro controller connected to the memory unit, the display unit, and the wireless connection unit, the micro controller configured to determine an adjustment of a gastric band for a patient by analyzing satiety state data of the patient and weight loss data of the patient, wirelessly receive gastric band pressure data for the gastric band, display a gastric band pressure chart on the display unit based on the gastric band pressure data, wirelessly receive weight data for the patient, display a weight chart on the display unit based on the weight data, wirelessly receive glucose data, and display a glucose chart on the display unit based on the glucose data.

In yet another embodiment, the present invention is a method for displaying gastric band information including determining an adjustment of the gastric band for a patient, wirelessly receiving gastric band pressure data for the gastric band, displaying a gastric band pressure chart on a display unit based on the gastric band pressure data, wirelessly receiving weight data for the patient, and displaying a weight chart on the display unit based on the weight data.

In still yet another embodiment, the present invention is a method for displaying gastric band information including determining an adjustment of the gastric band for a patient, wirelessly receiving gastric band pressure data for the gastric band, displaying a gastric band pressure chart on a display unit based on the gastric band pressure data, wirelessly receiving glucose data for the patient, and displaying a glucose chart on the display unit based on the weight data.

In one embodiment, the present invention includes a portable gastric band information system for determining an adjustment in size to a gastric band. The system includes a wireless connection unit, and a micro controller connected to the wireless connection unit. The micro controller is configured to wirelessly receive satiety state data of a patient, weight loss data of the patient, and gastric band pressure data for the gastric band, and determine an adjustment for the gastric band based on the satiety state data of the patient, the weight loss data of the patient, and the gastric band pressure data for the gastric band. Thereafter, the micro controller may wirelessly transmit the adjustment for the gastric band to the gastric band. In one embodiment, the adjustment may be a value indicating an amount of fluid to add to or remove from an inflatable portion of the gastric band. In another embodiment, the adjustment may be a value indicating an amount to increase or decrease an inner diameter of the gastric band. For example, the adjustment may be sent to a motor to increase or decrease an inner diameter of the gastric band.

DETAILED DESCRIPTION

Figure 1:
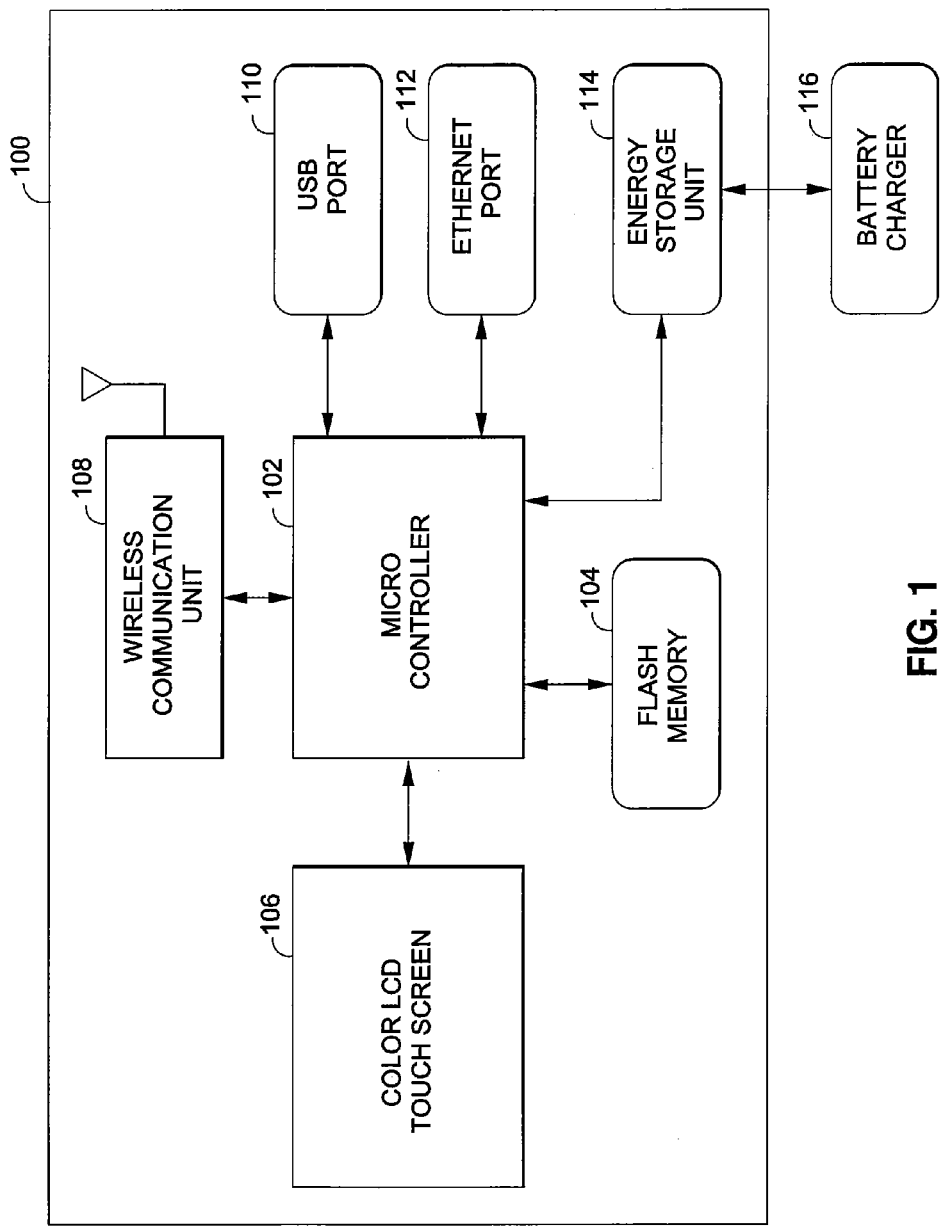
FIG. 1 illustrates a box diagram of a gastric band information system according to an embodiment of the present invention.

In one embodiment, the present invention includes a band information system 100 as shown in FIG. 1. As can be seen, the band information system 100 can include, for example, a micro controller 102, a flash memory 104, a color liquid crystal display ("LCD") touch screen 106, a wireless communication unit 108, a universal serial bus ("USB") port 110, an Ethernet port 112, and/or an energy storage unit 114. The band information system 100 can interface with a battery charger 116 to charge the energy storage unit 114.

The wireless communication unit 108 is connected, for example, to the micro controller 102. The wireless communication unit 108 can provide a wireless communication interface for the band information system 100. This can allow, for example, the band information system 100 to communicate with various computers and/or medical devices. The wireless communication unit 108 can be, for example, an RF link, a Bluetooth link, or any other type of device capable of providing a wireless communication interface for the band information system 100.

The USB port 110 is connected, for example, to the micro controller 102. The USB port 110 can provide, for example, a USB interface for the band information system 100 and allow the band information system 100 to communicate with various computers and/or medical devices.

The Ethernet port 112 is connected, for example, to the micro controller 102. The Ethernet port 112 can provide, for example, an Ethernet interface for the band information system 100 and allow the band information system 100 to communicate with various computers and/or medical devices.

The energy storage unit 114 can be connected, for example, to the micro controller 102. The energy storage unit 114 can interface, for example, to a battery charger 116 to increase its energy level. The energy storage unit 114 can supply power to the micro controller 102 and any other devices within the band information system 100.

The flash memory 104 can be connected, for example, to the micro controller 102. The flash memory 104 can store, for example, gastric band information that may be used by the micro controller 102. The gastric band information can be, for example, medical data such as gastric band pressure data, weight data, glucose data, blood pressure data, patient data, body mass index data, and/or gastric band implantation data. The medical data can be, for example, patient-specific medical data, which is medical data pertaining to a specific patient. The gastric band pressure data can indicate, for example, a pressure in a gastric band as real-time data, or historically. The weight data can indicate, for example, a weight of a patient as real-time data, or historically. The glucose data can indicate, for example, a glucose level of a patient as real-time data, or historically. The blood pressure data can indicate, for example, a blood pressure of the patient as real-time data, or historically. The gastric band implantation data can indicate, for example, gastric band volume data, gastric band implant date, gastric band implant type, and/or the gastric band pressure data. The gastric band volume data can indicate, the volume of the gastric band as real-time data, or historically. The gastric band information can also include, for example, patient data such as a name of the patient, a gender of the patient, an age of the patient, a birth date of the patient, and/or any other information relevant to the patient.

The color LCD touch screen 106 is connected, for example, to the micro controller 102. The color LCD touch screen 106 allows information to be displayed and also for a user to interact with the color LCD touch screen 106. Although a color LCD touch screen 106 is shown in FIG. 1, other types of screens may be used, such as monochrome screens. In addition, user interaction devices may be used in conjunction with the screen such as a keyboard, a mouse, or other types of device which can receive input from the user.

The micro controller 102 is connected, for example, to the flash memory 104, the color LCD touch screen 106, the wireless communication unit 108, the USB port 110, the Ethernet port 112, and/or the energy storage unit 114. The micro controller 102 can perform various processes to display gastric band information on the color LCD touch screen 106. The micro controller 102 can also receive various information from the color LCD touch screen 106 based on a user's interaction with the color LCD touch screen 106.

Figure 2:
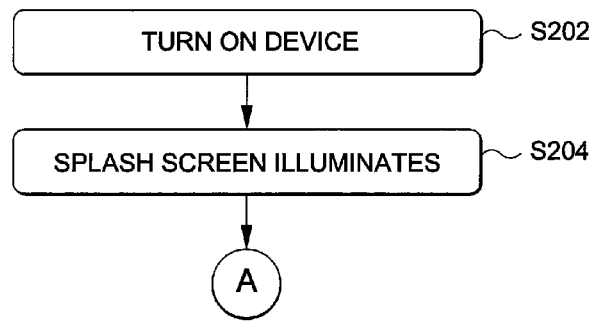
FIG. 2 illustrates a process according to an embodiment of the present invention.
Figure 3:
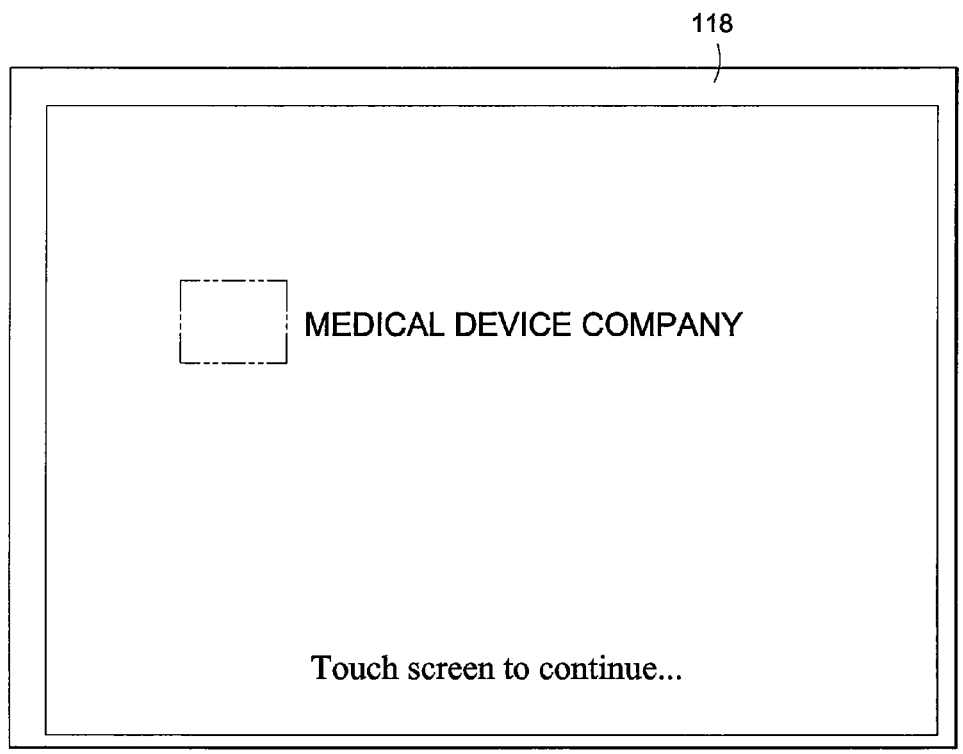
FIG. 3 illustrates a display screen according to an embodiment of the present invention.

For example, in one embodiment, the micro controller 102 and/or the band information system 100 can perform a process shown in FIG. 2. In Step S202, a device is turned on. For example, the band information system 100 can be turned on. In Step S204, a splash screen can be illuminated. For example, the micro controller 102 can instruct a splash screen to be illuminated in the color LCD touch screen 106. The splash screen can be, for example, the splash screen 118 as shown in FIG. 3. After Step S204, the process can proceed to section A, which is shown, for example, in FIG. 4.

Figure 4:
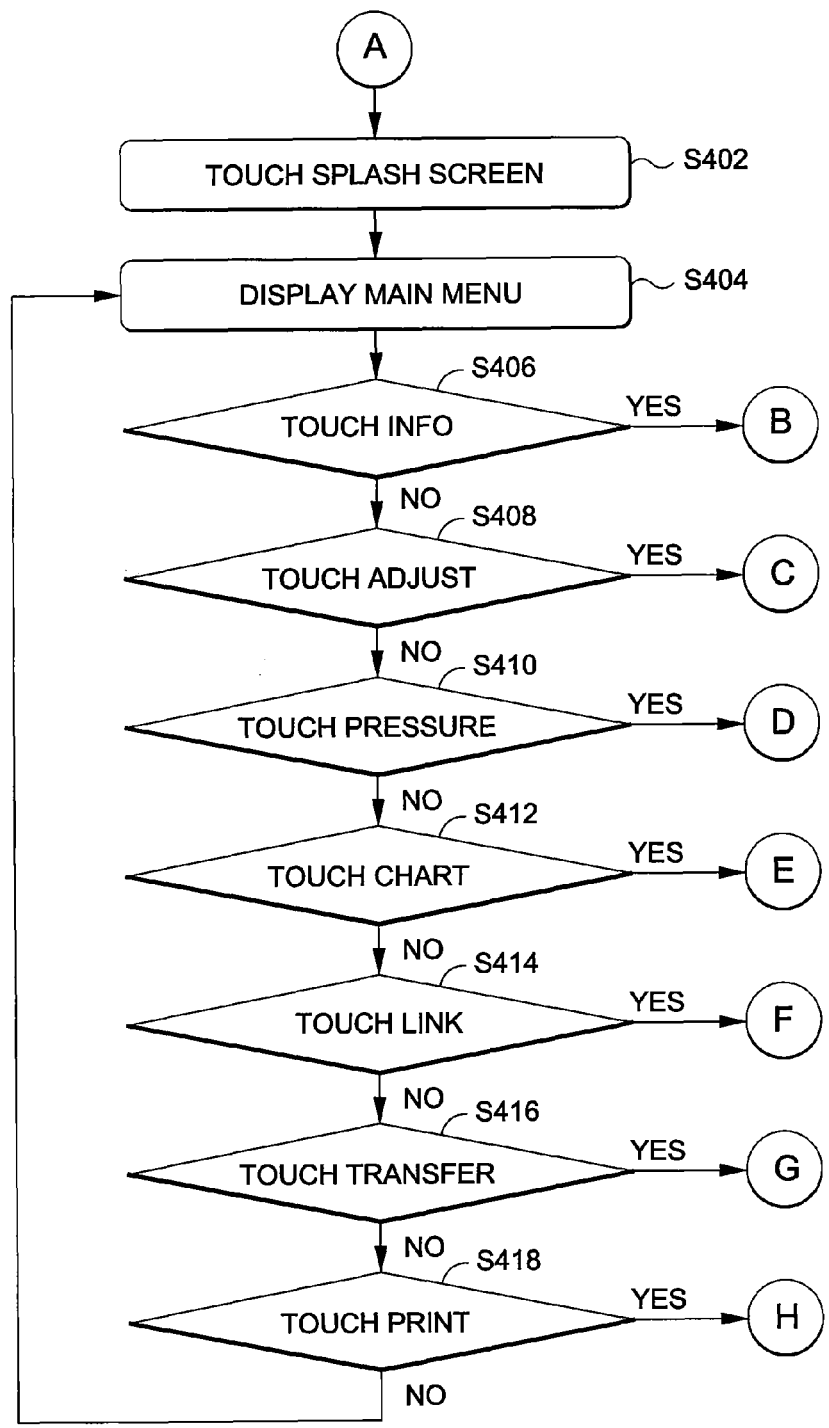
FIG. 4 illustrates a process according to an embodiment of the present invention.
Figure 5:
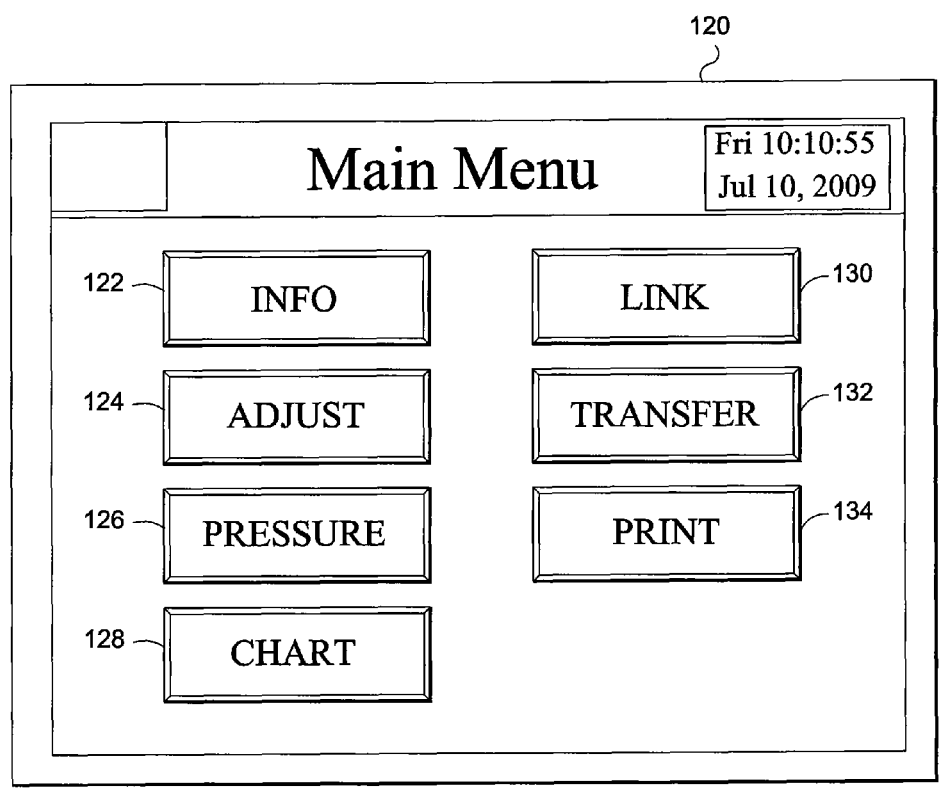
FIG. 5 illustrates a display screen according to an embodiment of the present invention.

As seen in FIG. 4, in Step S402, a splash screen 118 is touched (see also FIG. 3). For example, to continue the user touches the splash screen 118. This can be detected, for example, by the color LCD touch screen 106. In Step S404, a main menu can be displayed. For example, the micro controller can instruct the color LCD touch screen 106 to display a main menu 120 as shown in FIG. 5. The main menu 120 can include, for example, an info button 122, an adjust button 124, a pressure button 126, a chart button 128, a link button 103, a transfer button 132, and/or a print button 134.

In Step S406, a determination is made as to whether the info button 122 was touched. For example, the micro controller 102 can determine whether the info button 122 was touched in the main menu 120 displayed on the color LCD touch screen 106. If the info button 122 was touched, the process proceeds to section B, which will be described later. Otherwise, the process proceeds to Step S408.

In Step S408, a determination is made as to whether the adjust button 124 was touched. For example, the micro controller 102 can determine whether the adjust button 124 was touched in the main menu 120 displayed on the color LCD touch screen 106. If the adjust button 124 was touched, the process proceeds to section C, which will be described later. Otherwise, the process proceeds to Step S410.

In Step S410, a determination is made as to whether the pressure button 126 was touched. For example, the micro controller 102 can determine whether the pressure button 126 was touched on the main menu 120 displayed on the color LCD touch screen 106. If the pressure button 126 was touched, the process continues to section D. Otherwise, the process continues to Step S412.

In Step S412, a determination is made as to whether the chart button 128 was touched. For example, the micro controller 120 can determine whether the chart button 128 was touched on the main menu 120 displayed on the color LCD touch screen 106. If the chart button 128 was touched, the process continues to section E. Otherwise, the process continues to Step S414.

In Step S414, a determination is made as to whether the link button 130 was touched. For example, the micro controller 120 can determine whether the link button 130 was touched on the main menu 120 displayed on the color LCD touch screen 106. If the link button 130 was touched, the process continues to section F. Otherwise, the process continues to Step S416.

In Step S416, a determination is made as to whether the transfer button 132 was touched. For example, the micro controller 120 can determine whether the transfer button 132 was touched on the main menu 120 displayed on the color LCD touch screen 106. If the transfer button 132 was touched, the process continues to section G. Otherwise, the process continues to Step S418.

In Step S418, a determination is made as to whether the print button 134 was touched. For example, the micro controller 120 can determine whether the print button 134 was touched on the main menu 120 displayed on the color LCD touch screen 106. If the print button 134 was touched, the process continues to section H. Otherwise, the process repeats at Step S404.

Figure 6:
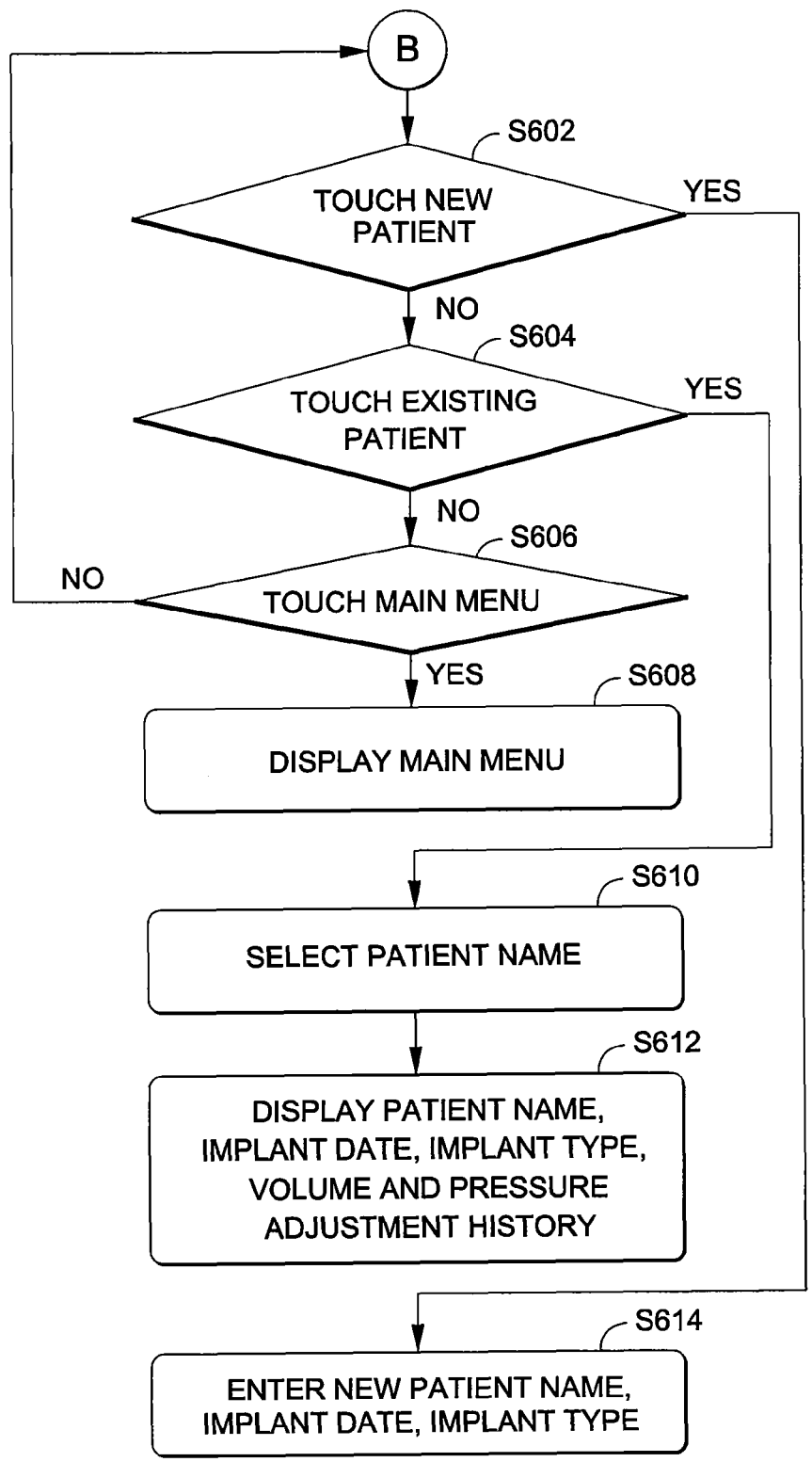
FIG. 6 illustrates a process according to an embodiment of the present invention.

The process for section B can be seen, for example, in FIG. 6. In the section B, a color LCD touch screen 106 can display, for example, a screen including a new patient button, an existing patient button, and/or a main menu button. In Step S602, a determination is made as to whether a new patient button has been touched. For example, the micro controller 102 determines whether the new patient button was touched on the color LCD touch screen 106. If the new patient was touched, the process proceeds to Step S614. Otherwise the process proceeds to Step S604.

In Step S614, a screen is displayed prompting a user to input a new patient name, an implant date, and/or an implant type. For example, the micro controller 102 can instruct the color LCD touch screen 106 to display a screen to prompt the user to input a new patient name, an implant date of the gastric band, and/or a type of gastric band implanted in the patient.

In Step S604, a determination is made as to whether the existing patient button was touched. For example, the micro controller 102 determines whether the existing patient button was touched on the color LCD touch screen 106. If the existing patient button was touched, the process proceeds to Step S610. Otherwise, the process proceeds to Step S606.

In Step S610, a user selects a patient name. For example, a list of patient names is displayed on the color LCD touch screen 106. The user selects one of the patient names on the color LCD touch screen 106. The process then proceeds to Step S612.

In Step S612, a patient name, an implant date, an implant type, and a volume and pressure adjustment history are displayed. For example, the micro controller 102 can instruct the color LCD touch screen 106 to display the patient name, the implant date of the gastric band, the implant type of the gastric band, and/or the volume and pressure adjustment history of the gastric band. The micro controller 102 can receive the patient name, the implant date of the gastric band, the implant type of the gastric band, and/or the volume and pressure adjustment history of the gastric band, for example, from the flash memory 104, and/or a computer separate from the gastric band information system 100.

In Step S606, a determination is made as to whether the main menu button was touched. For example, the micro controller 102 can determine whether the main menu button was touched in the color LCD touch screen 106. If the main menu button was touched, the process proceeds to Step S608. Otherwise, the process proceeds back to Step S602.

In Step S608, a main menu screen is displayed. For example, the micro controller 102 can instruct the color LCD touch screen 106 to display the main menu 120, as shown in FIG. 5. In one embodiment, once the main menu 120 is displayed, the process can proceed to Step S406 in FIG. 4.

Figure 7:
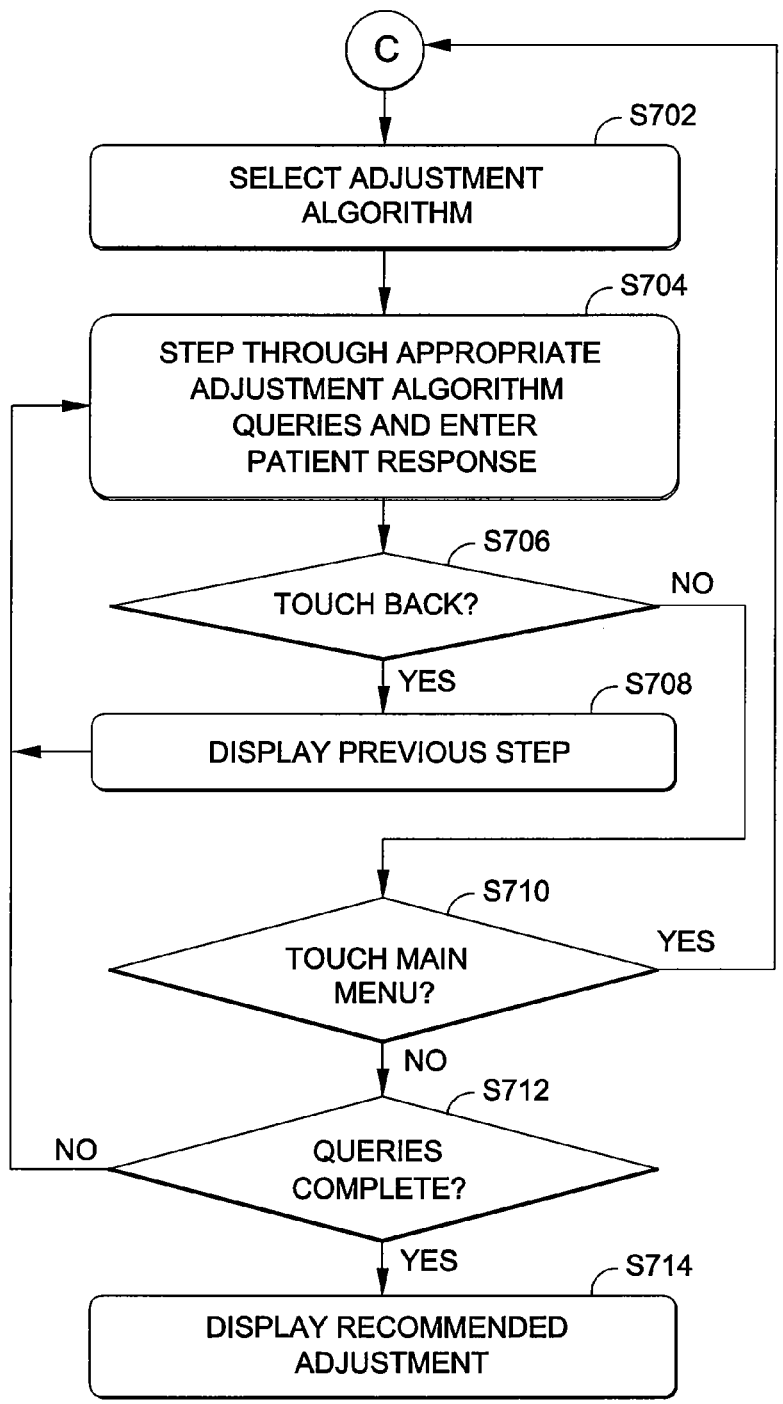
FIG. 7 illustrates a process according to an embodiment of the present invention.
Figure 8:
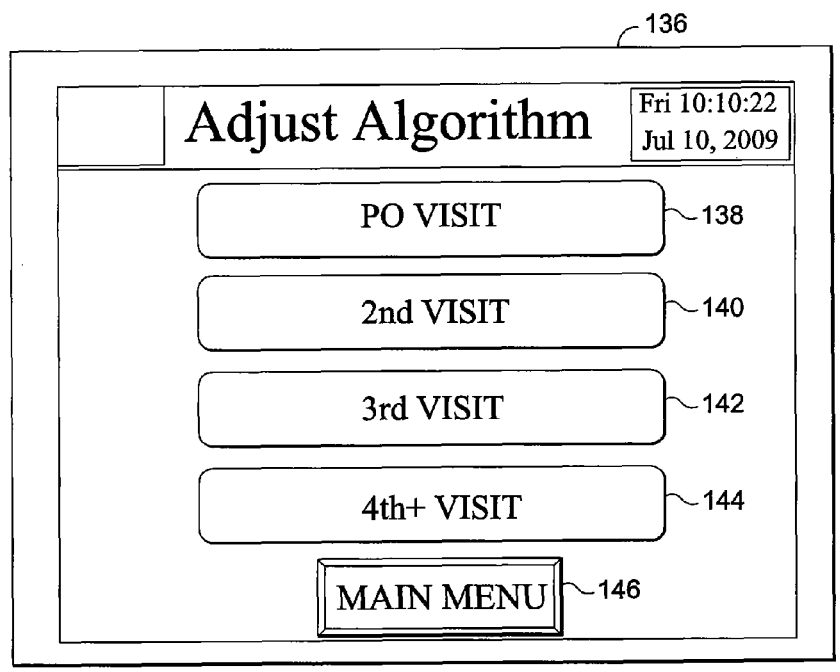
FIG. 8 illustrates a display screen according to an embodiment of the present invention.

The process for section C can be seen, for example, in FIG. 7. In section C, the micro controller 102 can display the adjust algorithm screen 136 as shown in FIG. 8. The adjust algorithm screen can include, for example, P0 or first, second, third, and fourth+visit buttons 138, 140, 142, and 144. In Step S702, an adjustment algorithm is selected. For example, the micro controller 102 can select an appropriate adjustment algorithm. In one embodiment, the micro controller 102 can receive a user input to determine the appropriate adjustment algorithm, or receive the appropriate adjustment algorithm from a computer. This can allow the best practice adjustment algorithm to be used. The micro controller 102 can, for example, wirelessly receive the appropriate adjustment algorithm from a computer. The appropriate adjustment algorithm can also be dependent for example, on which one of the visit buttons 138, 140, 142, and/or 144 is selected. The process then proceeds to Step S704.

Figure 9:
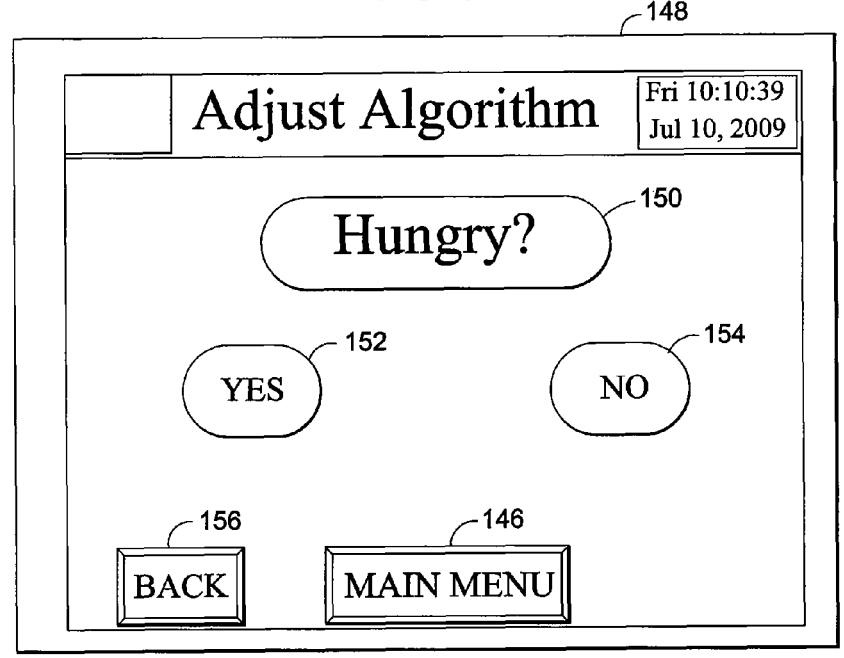
FIG. 9 illustrates a display screen according to an embodiment of the present invention.

In Step S704, the appropriate adjustment algorithm queries are presented and the patient response is entered. For example, after the user has selected one of the visit buttons 138, 140, 142, or 144, a satiety state screen 148 is displayed on the color LCD touch screen 106 as shown in FIG. 9. The satiety state screen 148 can display a query 150, inputs 152 and 154, a back button 156, and the main menu button 146. In FIG. 9, the query asks whether the patient is hungry or not. The input 152 indicates that the patient is hungry, while the input 154 indicates that the patient is not hungry. The inputs 152 and 154 can be used as satiety state data. Satiety state data can be, for example, hunger state data. This can be real-time data as to whether the patient is hungry or not.

Figure 10:
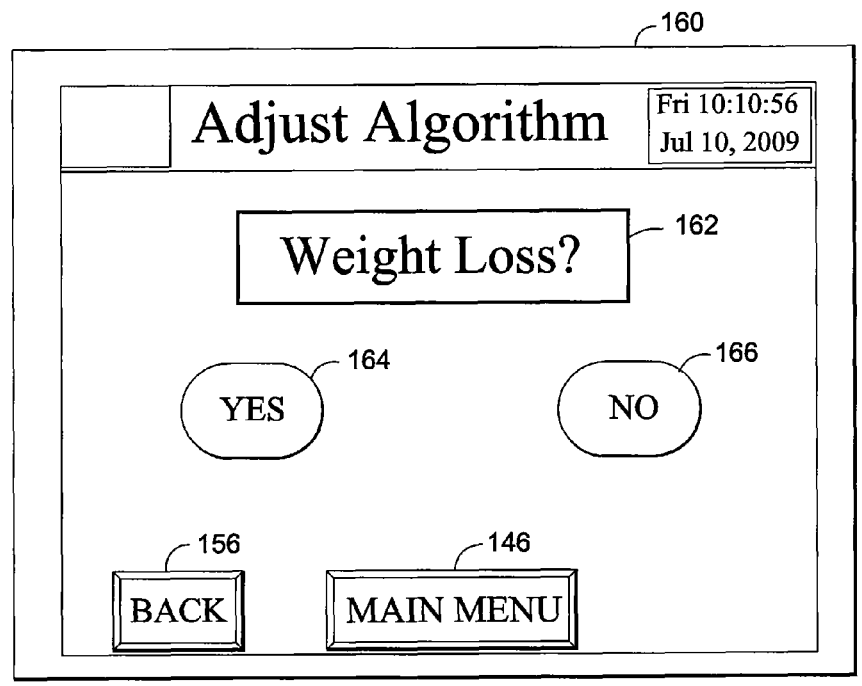
FIG. 10 illustrates a display screen according to an embodiment of the present invention.

After the user selects input 152 or input 154, the process displays a weight loss screen 160 on the color LCD touch screen 106 as shown in FIG. 10. The weight loss screen 160 can display a query 162, inputs 164 and 166, the back button 156, and the main menu button 146. In FIG. 10, the query asks whether the patient has lost weight or not. The input 164 indicates that the patient has lost weight, while the input 166 indicates that the patient has not lost weight. The inputs 164 and 166 can be used as weight loss data.

In Step S706, a determination is made as to whether a back button has been touched. For example, the micro controller 102 can determine if the back button 156 in the satiety state screen 148 (FIG. 9) or the back button 156 in the weight loss screen 160 (FIG. 10) has been touched on the color LCD touch screen 106. If the back button was touched, the process proceeds to Step S708. Otherwise the process continues to Step S710.

In Step S708, a previous step is displayed. For example, if the back button 156 in the satiety state screen 148 was touched, the previous screen, or the adjust algorithm screen 136, is displayed on the color LCD touch screen 106. If the back button 156 in the weight loss screen 160 was touched, the previous screen, or the satiety state screen 148, is displayed on the color LCD touch screen 106. Thus, the back button 156 allows the user to view the previous screen. The process then proceeds to Step S704 and allows the process to continue with the previous screen.

In Step S710, a determination is made as to whether the main menu button was touched. For example, the micro controller 102 can determine whether the main menu button 146 in the satiety state screen 148 or the weight loss screen 160 was touched. If the main menu button was touched, the process continues, for example, to Step S404 in FIG. 4. Otherwise, the process continues to Step S712.

In Step S712, a determination is made as to whether the query is complete. For example, after the satiety state screen 148, the query would not be complete since the weight loss screen 160 still needs to be displayed. However, after the weight loss screen 160, the query would be complete. If the query is not complete, the process repeats at Step S704. Otherwise, if the query is complete, the process continues to Step S714.

Figure 11:
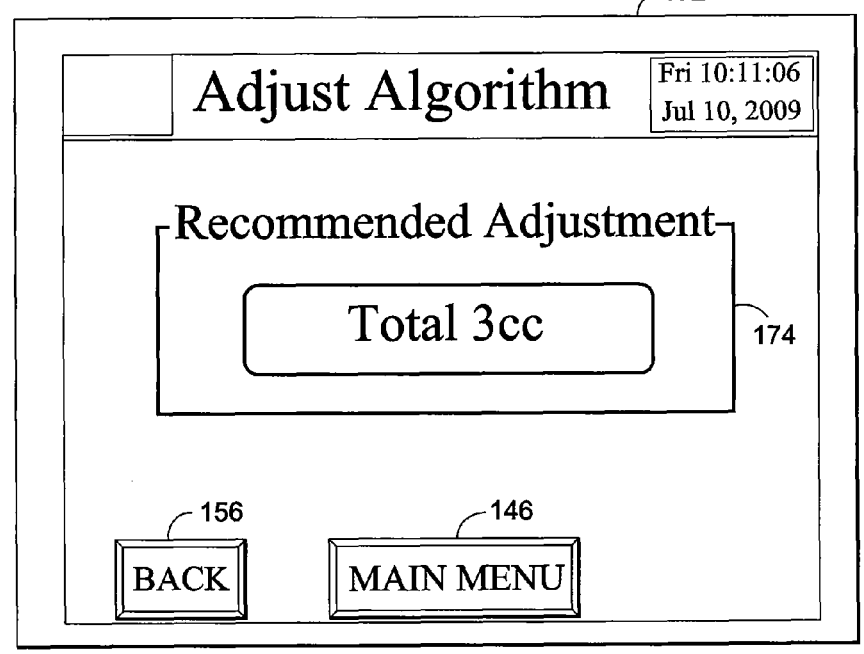
FIG. 11 illustrates a display screen according to an embodiment of the present invention.

In Step S714, a recommended adjustment is displayed. For example, based on the satiety state data, and the weight loss data, the micro controller 102 can determine a recommended adjustment. The recommended adjustment can be displayed, for example, as a recommended adjustment screen 172 on the color LCD touch screen 106 as shown in FIG. 11. The adjustment screen 172 can indicate a recommended adjustment amount 174. The recommended adjustment amount 174 can indicate how much fluid to add or subtract from the gastric band in the patient in order to tighten or loosen the gastric band.

The micro controller 102 can also wirelessly transmit the recommended adjustment to a gastric band and/or control the gastric band to tighten or loosen based on the recommended adjustment. The micro controller 102 can also wirelessly transmit the recommended adjustment to a syringe and/or control the syringe to tighten or loosen the gastric band based on the recommended adjustment. In one embodiment, the wireless controller 102 can also use gastric band pressure data to determine the recommended adjustment.

Figure 12:
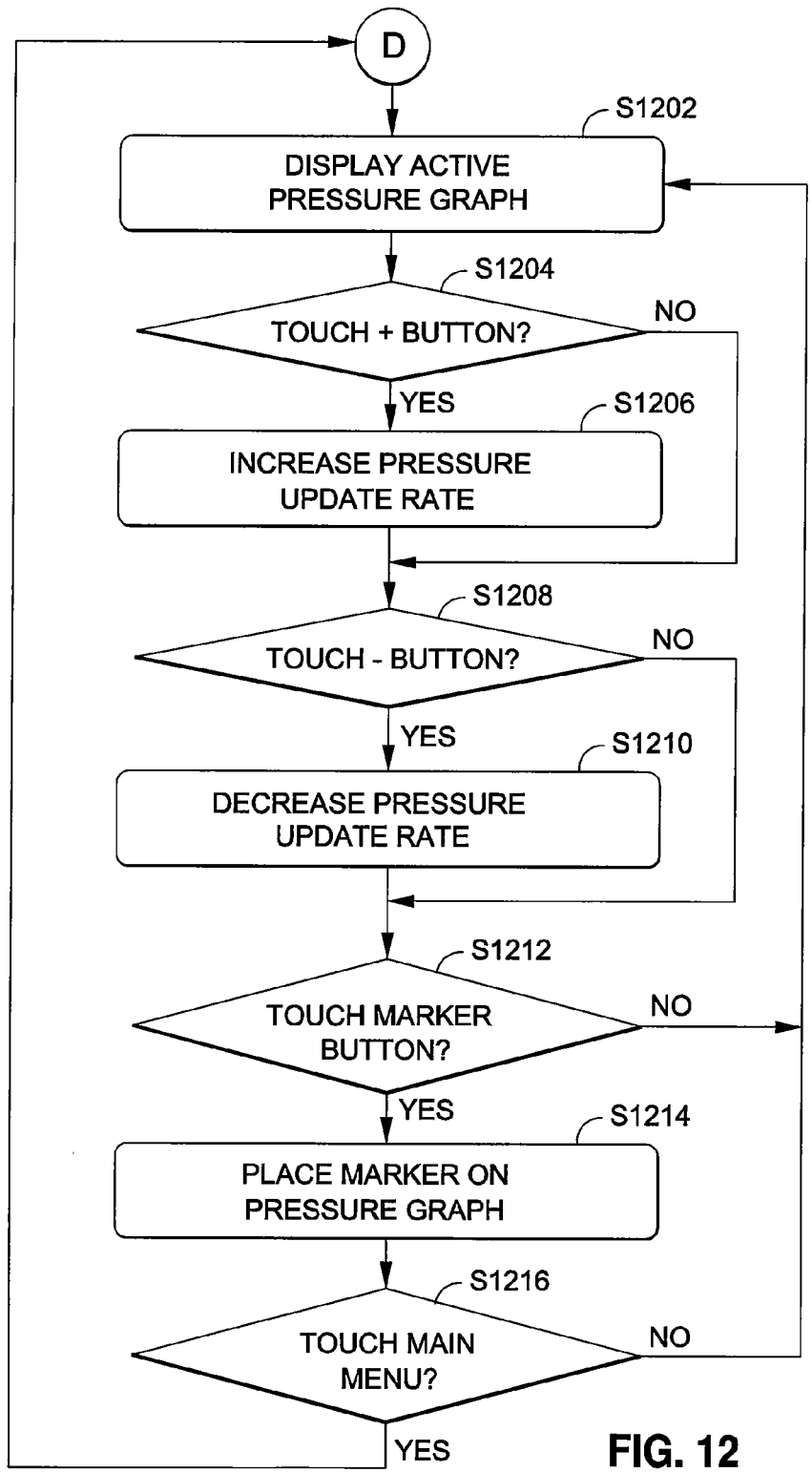
FIG. 12 illustrates a process according to an embodiment of the present invention.
Figure 13:
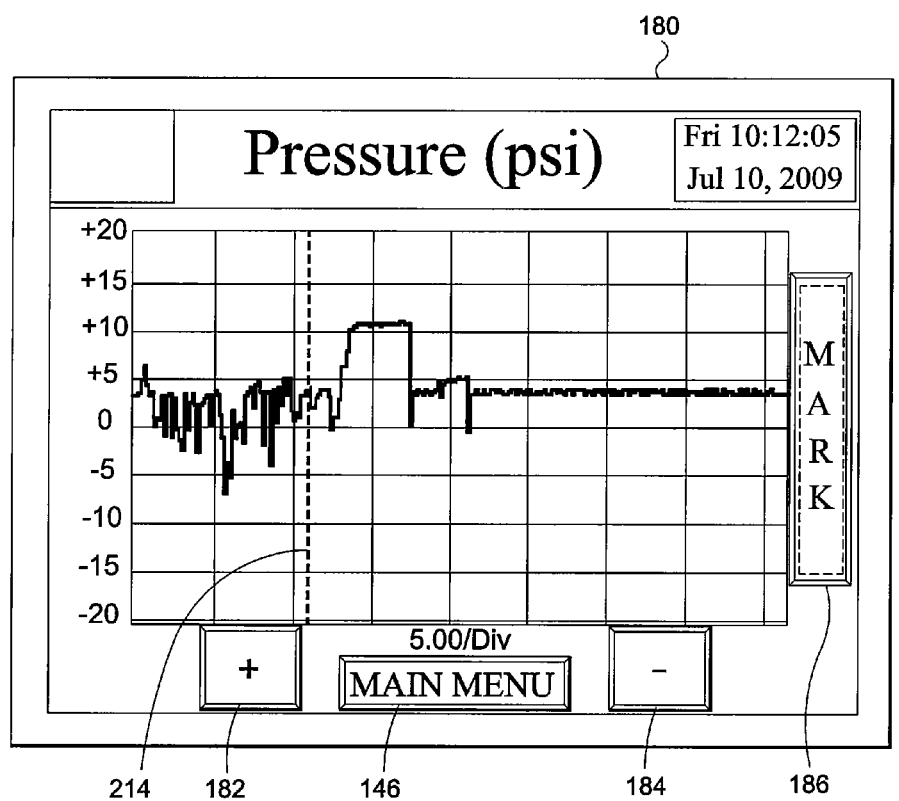
FIG. 13 illustrates a gastric band pressure chart according to an embodiment of the present invention.

The process for section D can be seen, for example, in FIG. 12. In Step S1202, an active pressure graph can be displayed. For example, the micro controller 102 can control the color LCD touch display screen 106 to display an active pressure graph such as a gastric band pressure chart 180 as seen in FIG. 13. The gastric band pressure chart 180 can display, for example, gastric band pressure information based on gastric band pressure data. The gastric band pressure data can be historical data, and/or real-time data. Thus, for example, the gastric band pressure data can indicate peristalsis in real-time. The gastric band pressure data can be received, for example, by the micro controller 102 from a gastric band pressure monitoring unit. The gastric band pressure data can be received, for example, in a wired manner through, for example, the USB port 110 and/or the Ethernet port 112. The gastric band pressure data can also be received, for example, wirelessly from the wireless communication unit 108. The gastric band pressure chart can include, for example, a marker button 186, a plus button 182, a minus button 184, and/or a main menu button 146.

In Step S1204, a determination is made as to whether the plus button 182 was touched. For example, the micro controller 102 can determine whether the plus button 182 on the gastric band pressure chart 180 was touched. If the plus button 182 was touched, the process proceeds to step S1206. Otherwise, the process proceeds to Step S1208.

In Step S1206, a pressure update rate is increased. For example, the frequency with which the gastric band pressure data is received can be increased. Furthermore, for example, the resolution of the gastric band information displayed on the gastric band chart 180 can be increased.

In Step S1208, a determination is made as to whether the minus button 184 was touched. For example, the micro controller 102 can determine whether the minus button 184 on the gastric band pressure chart 180 was touched. If the minus button 184 was touched, the process proceeds to Step S1210. Otherwise, the process proceeds to Step S1212.

In Step S1210, a pressure update rate is decreased. For example, the frequency with which the gastric band pressure data is received can be decreased. Furthermore, for example, the resolution of the gastric band information displayed on the gastric band chart 180 can be decreased.

In Step S1212, a determination is made as to whether a marker button was touched. For example, the micro controller 102 can determine whether the marker button 186 on the gastric band pressure chart 180 was touched. If the market button was touched, then the process proceeds to Step S1212. Otherwise, the process repeats at Step S1202.

In Step S1212, a marker 214 is placed on the pressure graph. For example, the micro controller 102 places a marker 214 on the gastric band pressure chart 180. The process then proceeds to Step S1216. In Step S1216, a determination is made as to whether the main menu button 146 was touched. For example, the micro controller 102 determines whether the main menu button 146 on the gastric band pressure chart 180 was touched. If the main menu button 146 was touched, the process proceeds to Step S404 in FIG. 4. Otherwise, the process repeats at Step S1202.

Figure 14:
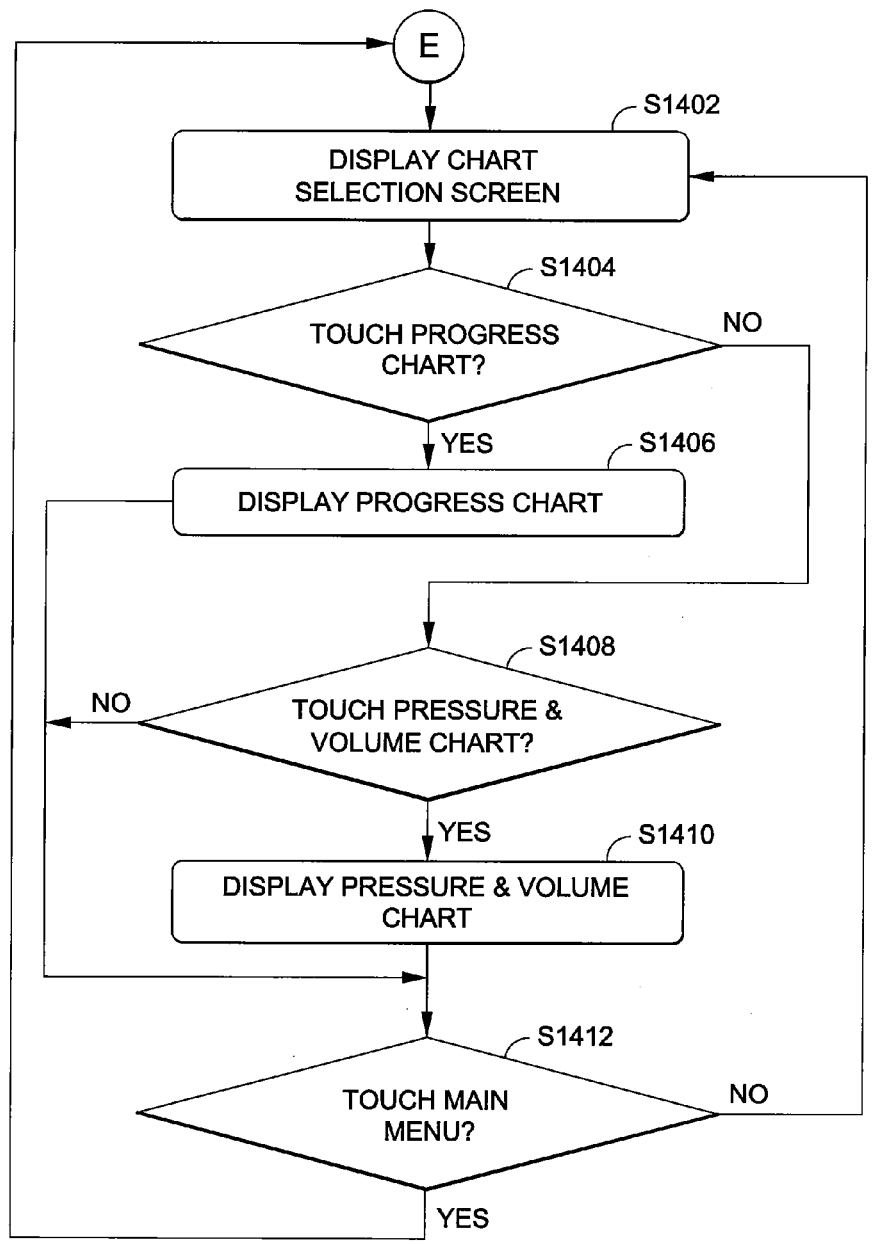
FIG. 14 illustrates a process according to an embodiment of the present invention.
Figure 15:
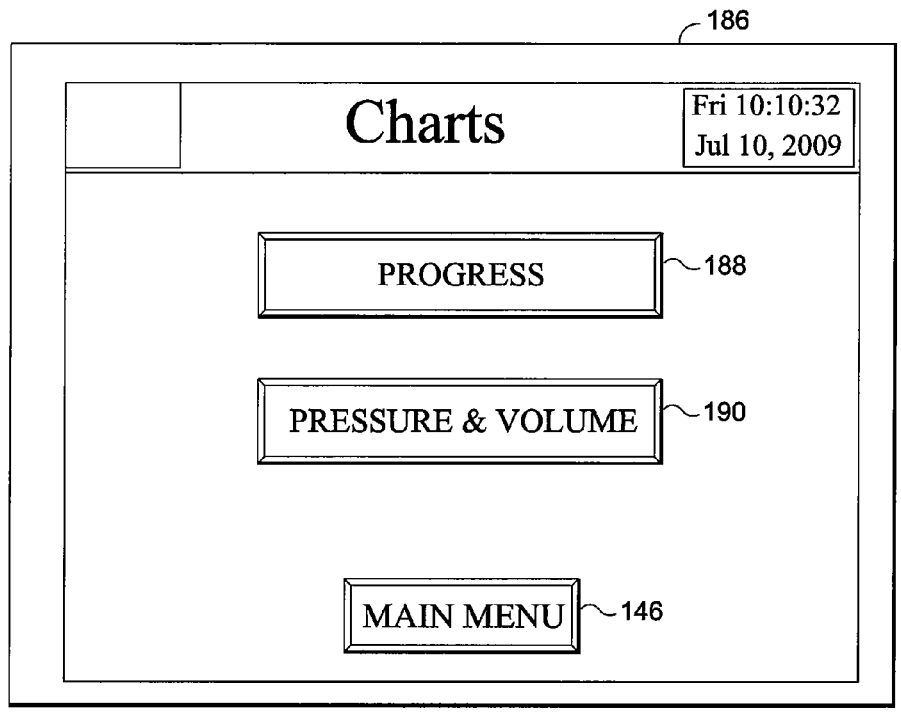
FIG. 15 illustrates a display screen according to an embodiment of the present invention.

The process for section E can be seen, for example, in FIG. 14. In Step S1402, a chart selection screen is displayed. For example, a chart selection screen 186 (see also FIG. 15) can be displayed on the color LCD touch screen 106. The chart selection screen 186 includes, for example, a progress chart button 188, a pressure and volume chart button 190, and a main menu button 146.

In Step S1404, a determination is made as to whether a progress chart button 188 was touched. For example, the micro controller 102 can determine whether the progress chart button 188 was touched. If the progress chart button 188 was touched, the process proceeds to Step S1406. Otherwise, the process proceeds to Step S1408.

Figure 16:
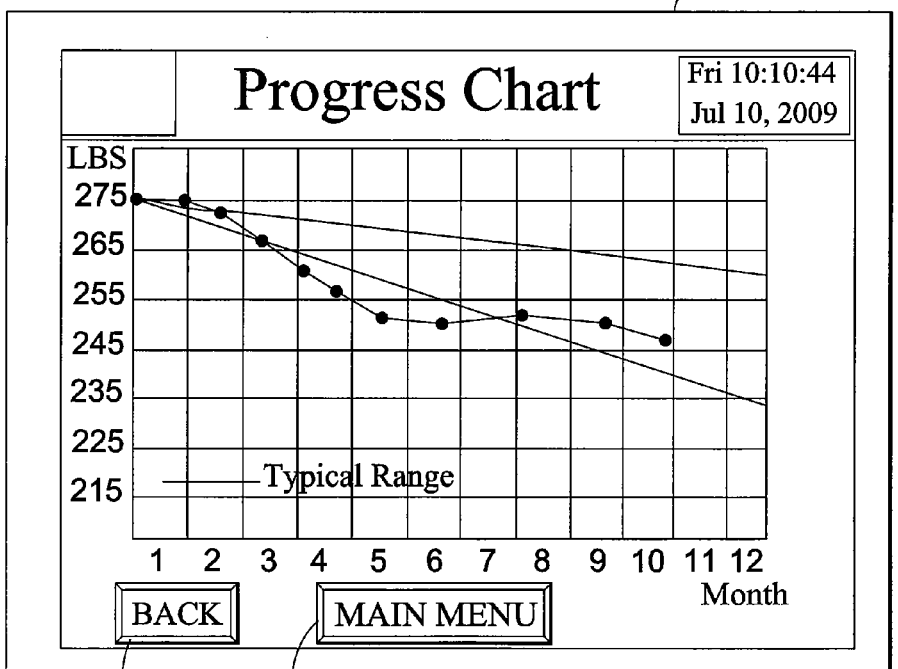
FIG. 16 illustrates a weight chart according to an embodiment of the present invention.

In Step S1406, the progress chart 192 is displayed. For example, the progress chart 192 is displayed on the color LCD touch screen 106 as seen in FIG. 16. The progress chart 192 can be, for example, a weight chart and be based, for example, on weight data for the patient. For example, the progress chart 192 displays the weight of the patient charted over several months. The progress chart 192 also displays a typical range of the weight. Thus, the user and/or the patient can see the patient's progress in weight loss and also see how the patient's weight loss compares to a typical range of weight loss.

The micro controller 102 and/or the band information system 100 can receive the weight data from the flash memory 104 and/or a computer. The micro controller 102 and/or the band information system 100 can receive the weight data from the computer in a wired manner, for example, through the USB port 110 and/or the Ethernet port 112. The micro controller 102 and/or the band information system 100 can receive the weight data from the computer wirelessly, for example, through the wireless communication unit 108. The process then proceeds to Step S1412.

In Step S1408, a determination is made as to whether the pressure and volume chart button 190 was touched. For example, the micro controller 102 can determine whether the pressure and volume chart button 190 was touched. If the pressure and volume chart button 190 was touched, the process proceeds to Step S1410. Otherwise, the process continues to Step S1412.

Figure 17:
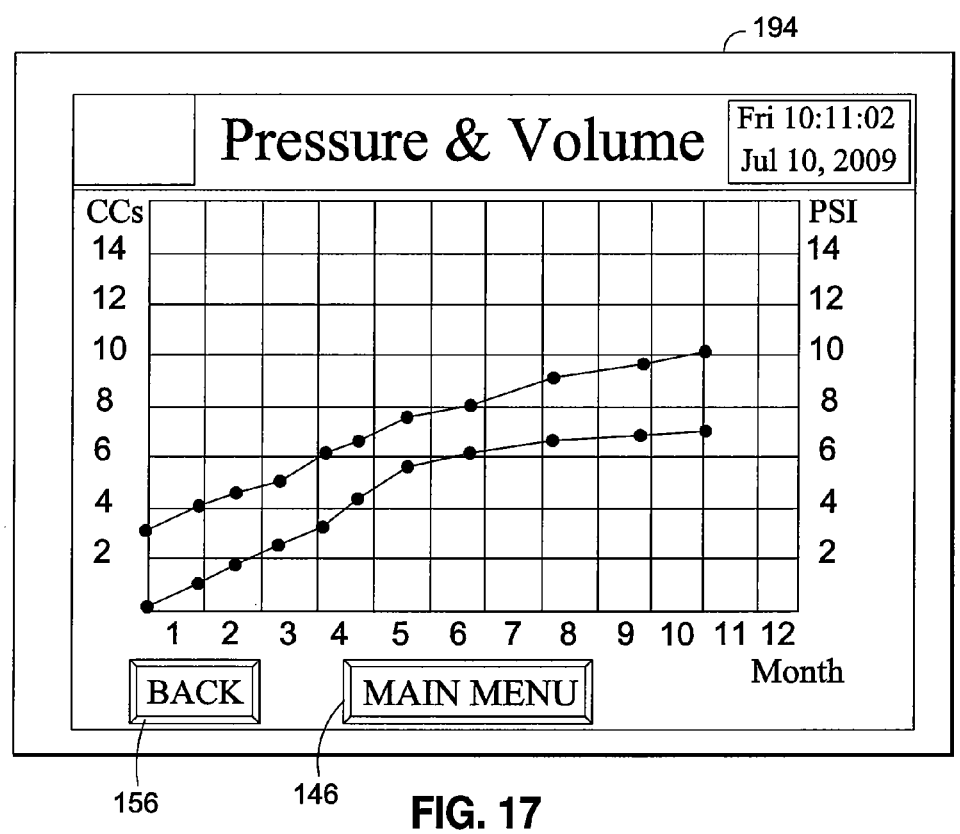
FIG. 17 illustrates a gastric band pressure chart and a gastric band volume chart according to an embodiment of the present invention.

In Step S1410, a pressure and volume chart 194 is displayed. For example, the pressure and volume chart 194 is displayed as shown in FIG. 17. The pressure and volume chart 194 can indicate, for example, a pressure and/or a volume of the gastric band in the patient. The process then proceeds to Step S1412.

In Step S1412, a determination is made as to whether a main menu button was touched. For example, the micro controller 102 can determine whether the main menu button 146 was touched in the progress chart 192 and/or the pressure and volume chart 194 was touched. If the main menu button 146 was touched, the process proceeds to Step S404 in FIG. 4. Otherwise, the process repeats at Step S1402. Optionally, the process can also detect whether the back button 156 in the progress chart 192 and/or the pressure and volume chart 194 was touched. If the back button 156 was touched, the previous screen can be displayed. For example, if the back button 156 was touched in the progress chart 192 and/or the pressure and volume chart 194 was touched, the previous screen, or the chart selection screen 186 can be displayed.

Figure 18:
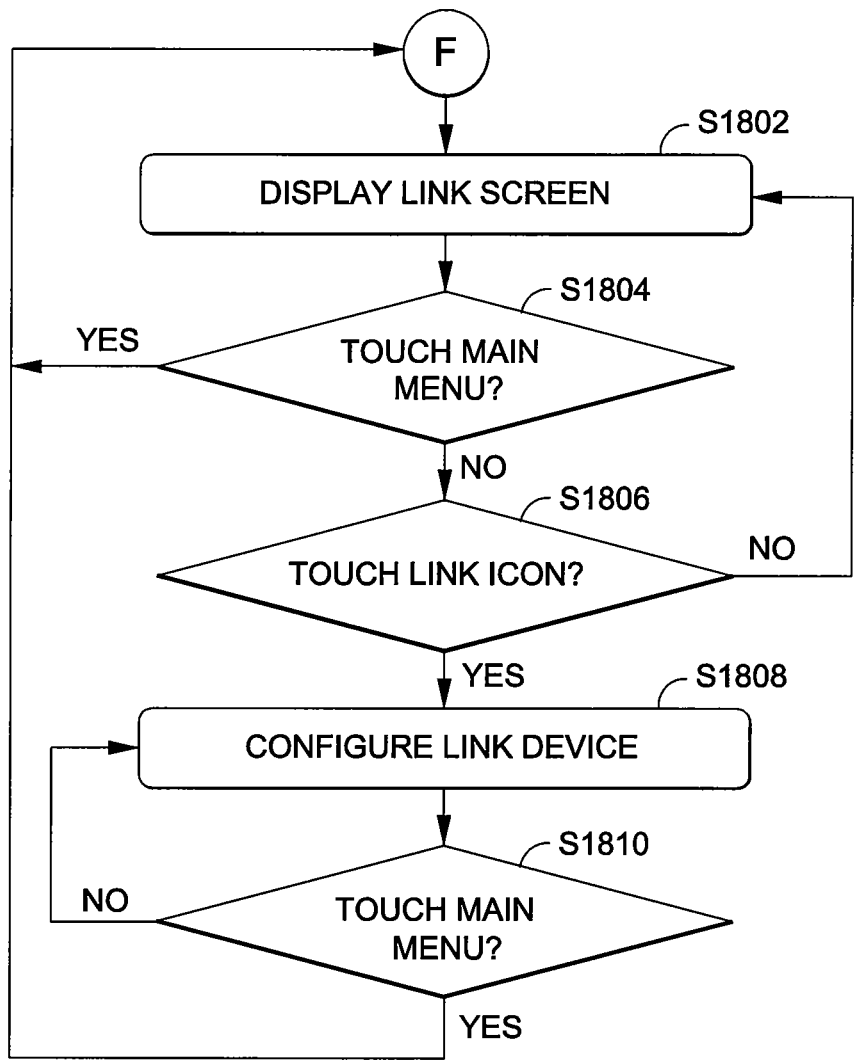
FIG. 18 illustrates a process according to an embodiment of the present invention.
Figure 19:
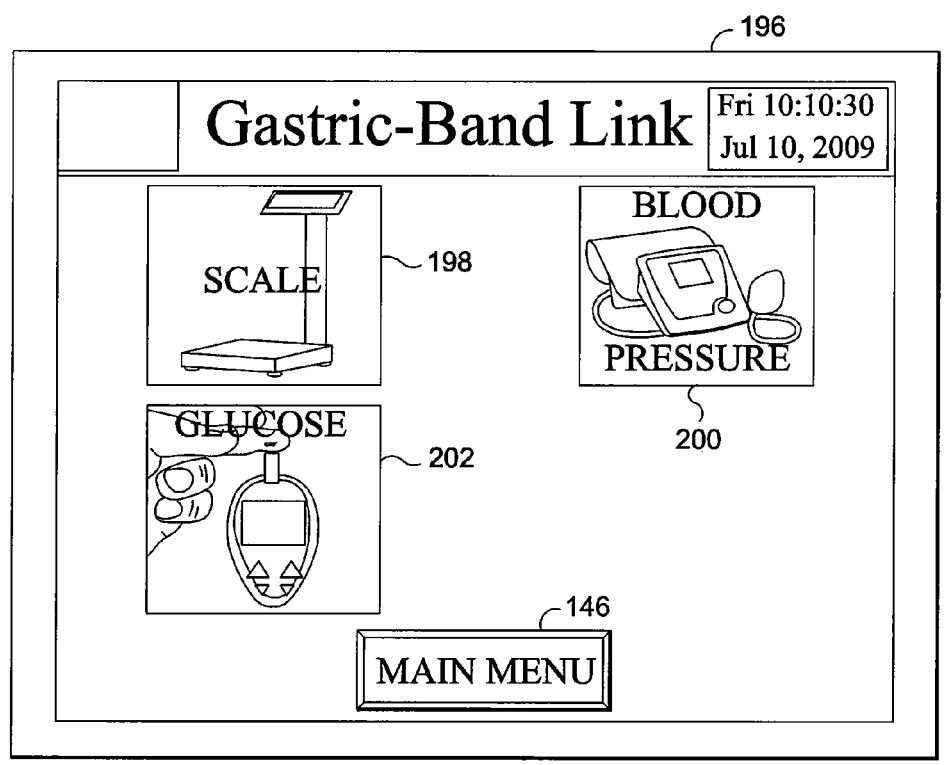
FIG. 19 illustrates a display screen according to an embodiment of the present invention.

The process for section F can be seen, for example, in FIG. 18. In Step S1802, a link screen 196 can be displayed. For example, the micro controller 102 can instruct the color LCD touch screen 106 to display a link screen 196 as shown in FIG. 19. The link screen 196 can include, for example, the main menu button 146, a link icon 198, a link icon 200, and/or a link icon 202. The link icon 198 can correspond, for example, to a connection with a weight monitoring unit, such as a scale. The link icon 200 can correspond, for example, to a connection with a blood pressure monitoring unit. The link icon 202 can correspond, for example, to a connection with a glucose monitoring unit.

In Step S1804, a determination is made as to whether the main menu button 146 was touched. If the main menu button was touched, the process proceeds to Step S404 in FIG. 4. Otherwise, the process proceeds to Step S1806. In Step S1806, a determination is made as to whether a link icon 200 was touched. For example, the micro controller 102 can determine whether the link icon 198, the link icon 200 or the link icon 202 was touched. If the link icon 198, the link icon 200 or the link icon 202 was touched, the process proceeds to Step S1808. Otherwise, the process repeats at Step S1802.

In Step S1808, a link device is configured. For example, a medical device can be configured to transfer medical data to the micro controller 102 and/or the band information system 100. The medical data can be used by the micro controller 102 and/or the band information system 100 to display a medical chart. For example, if the link icon 198 was touched, a weight monitoring unit can be configured to transfer weight data to the micro controller 102 and/or the band information system 100. The micro controller 102 and/or the band information system 100 can use the weight data to determine and/or display a weight chart on the color LCD touch screen 106.

If the link icon 200 was touched, a blood pressure monitoring unit can be configured to transfer blood pressure data to the micro controller 102 and/or the band information system 100. The micro controller 102 and/or the band information system 100 can use the blood pressure data to determine and/or display a blood pressure chart on the color LCD touch screen 106.

If the link icon 202 was touched, a glucose monitoring unit can be configured to transfer glucose data to the micro controller 102 and/or the band information system 100. The micro controller 102 and/or the band information system 100 can use the glucose data to determine and/or display a glucose data chart on the color LCD touch screen 106. The weight data, the blood pressure data, and/or the glucose data can be transferred to the micro controller 102 and/or the band information system 100 in a wired manner through the USB port 110 and/or the Ethernet port 112.

The weight data, the blood pressure data, and/or the glucose data can also be transferred to the micro controller 102 and/or the band information system 100 wirelessly through the wireless communication unit 108. The process then proceeds to Step S1810.

In Step S1810, a determination is made as to whether the main menu button 146 was touched. For example, the micro controller 106 can determine whether the main menu button 146 was touched. If the main menu button 146 was touched, the process proceeds to Step S404 in FIG. 4. Otherwise, the process repeats Step S1810 and the micro controller 102 and/or the band information system 102 can continue to receive medical data from the medical device.

Figure 20:
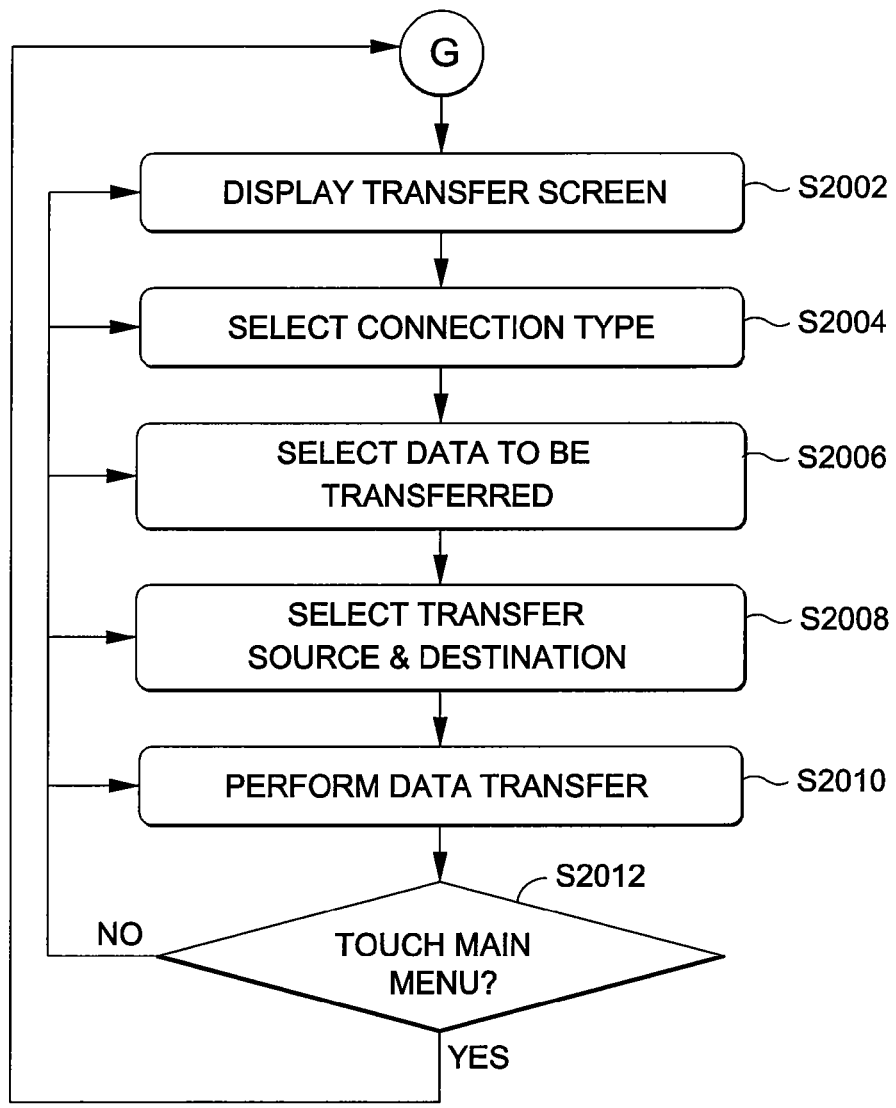
FIG. 20 illustrates a display screen according to an embodiment of the present invention.

The process for section G can be seen, for example, in FIG. 20. In Step S2002, a transfer screen is displayed. For example, a transfer screen can be displayed on the color LCD touch screen 106. In Step S2004, a connection type can be selected. For example, a wired connected such as through the USB port 110 and/or an Ethernet port 112 can be selected. A wireless connection such as through the wireless communication unit 108 can also be selected. In Step S2006, a type of data to be transferred can be selected. For example, the type of patient data and/or medical data to be transferred can be selected.

Figure 21:
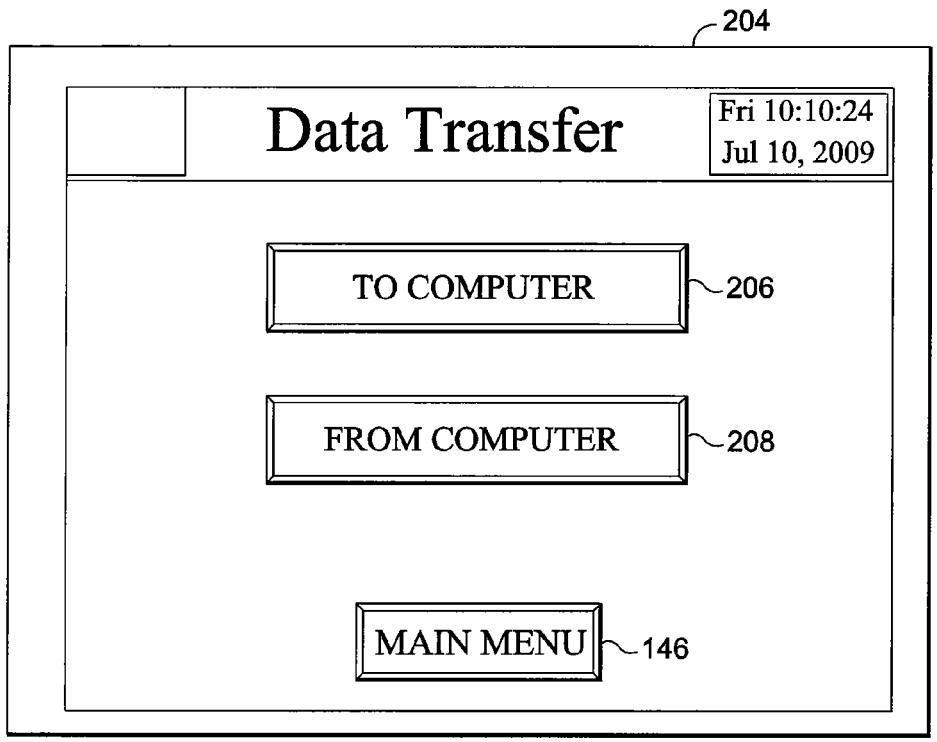
FIG. 21 illustrates a display screen according to an embodiment of the present invention.

In Step S2008, a transfer source and destination can be selected. For example, a transfer source and destination screen 204 can be displayed on the color LCD touch screen 106 as shown in FIG. 21. The transfer source and destination screen 204 can include, for example, a button 206, a button 208, and the main menu 146. The button 206 can correspond to the band information system 100 being the source and a computer being the destination. The button 208 can correspond to the computer being the source and the band information system 100 being the destination.

Figure 22:
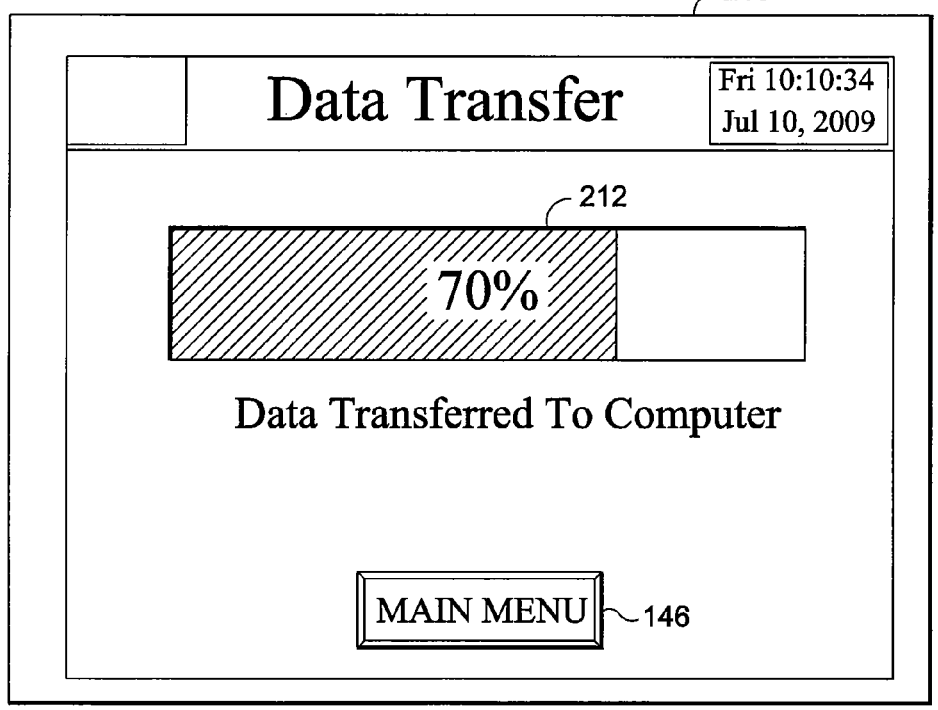
FIG. 22 illustrates a process according to an embodiment of the present invention.

In step S2010, a data transfer is performed. For example, the medical data can be transferred from the source to the destination. During the data transfer, a data transfer progress screen 210 can be displayed on the color LCD touch screen 106, as seen in FIG. 22. The data transfer progress screen 210 can include, for example, a data transfer progress 212 indicating the progress of the data transfer from the source to the destination, and/or the main menu button 146. In Step S2012, a determination is made as to whether a main menu button was touched. For example, the micro controller 102 can determine if the main menu button 146 was touched. If the main menu button 146 was touched, the process proceeds to Step S404 in FIG. 4. Otherwise, the process repeats at the appropriate step.

Figure 23:
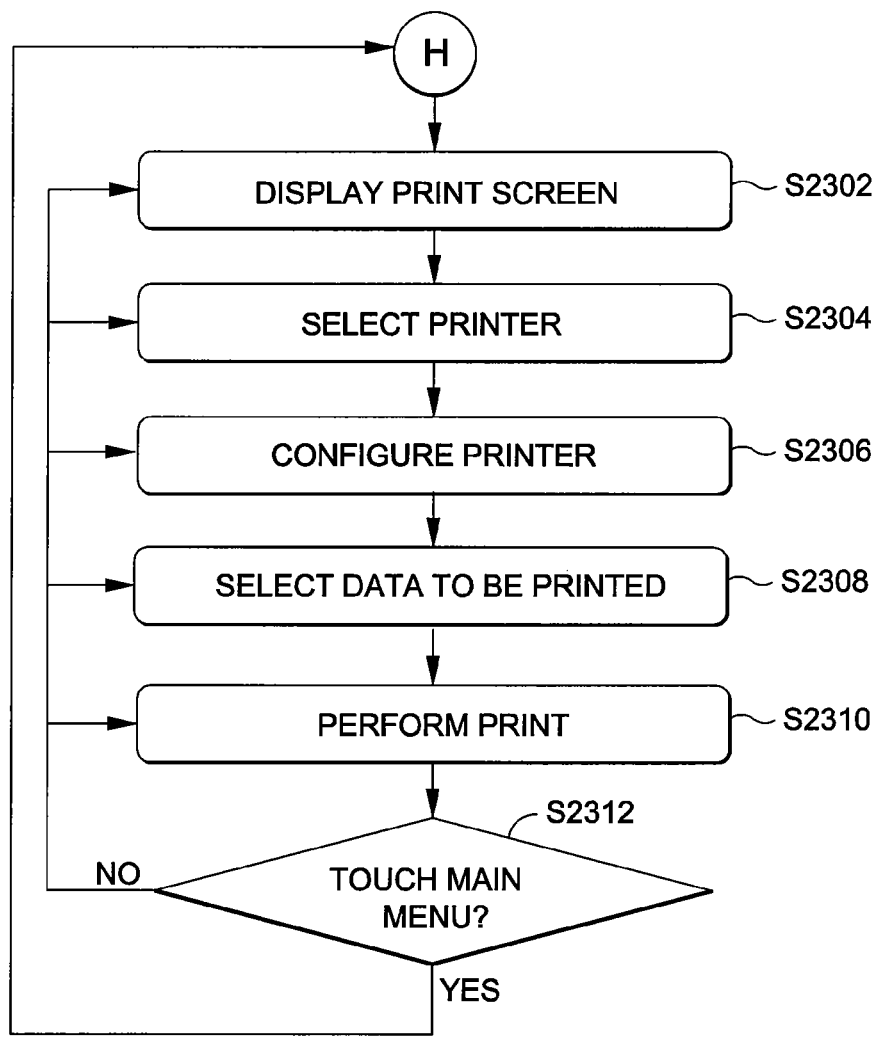
FIG. 23 illustrates a process according to an embodiment of the present invention.

The process for section H can be seen, for example, in FIG. 23. In Step S2302, a print screen can be displayed. For example, a print screen can be displayed on the color LCD touch screen 106. In Step S2304, a printer can be selected. For example, a printer can be automatically selected by the micro controller 102 or a user can select the printer. In Step S2306, a printer can be configured. For example, the micro controller 102 can configure the selected printer. In Step S2308, data to be printed is selected. For example, the user can select the patient data, the medical data, and/or the medical charts to be printed. In Step S2310 the printing can be performed. For example, the selected patient data, medical data, and/or medical charts can be printed. In Step S2312, a determination is made as to whether a main menu button was touched. If the main menu button was touched, the process proceeds to Step S404 in FIG. 4. Otherwise, the process repeats at the appropriate step.

Figure 24:
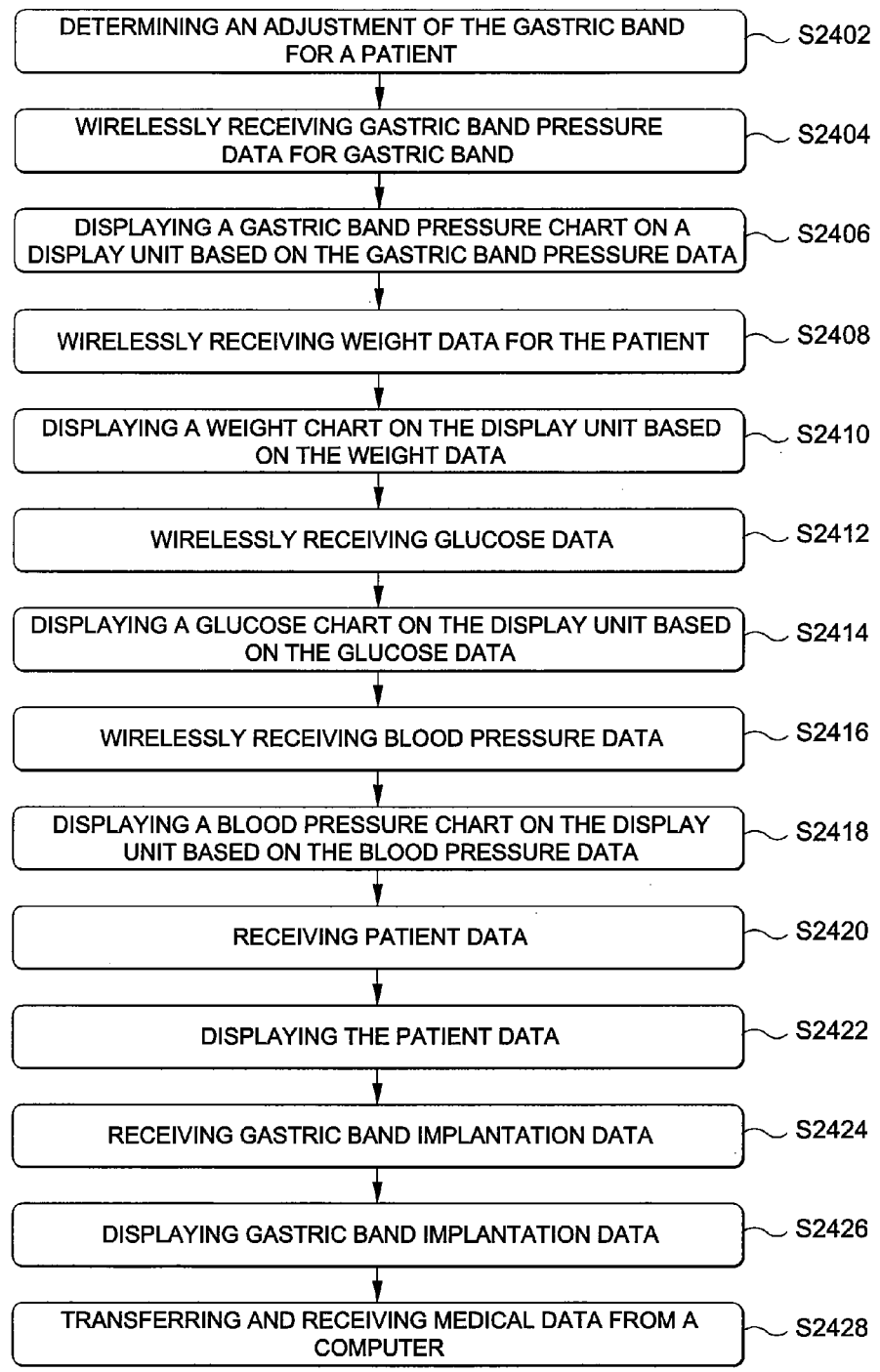
FIG. 24 illustrates a process according to an embodiment of the present invention.

In one embodiment, the present invention can also be a process as disclosed in FIG. 24. In Step S2402, an adjustment of the gastric band for a patient can be determined. For example, the micro controller 102 can determine an appropriate algorithm to use for the adjustment of the gastric band. In one embodiment, the satiety state data and the weight loss data is collected from the patient to determine the adjustment of the gastric band.

In Step S2404, the gastric band pressure data for the gastric band is wirelessly received. For example, the micro controller 102 can wirelessly receive gastric band pressure data from a gastric band pressure monitoring unit using the wireless communication unit 108. In Step S2406, a gastric band pressure chart is displayed on the display unit based on the gastric band pressure data. For example, a gastric band pressure chart is displayed on the color LCD touch screen 106 based on the gastric band pressure data.

In Step S2408, the weight data for the patient is wirelessly received. For example, the micro controller 102 can wirelessly receive the weight data from a weight monitoring unit using the wireless communication unit 108. In Step S2410, a weight chart is displayed on the display unit based on the weight data. For example, a weight chart is displayed on the color LCD touch screen 106 based on the weight data.

In Step S2412, the glucose data is wirelessly received. For example, the micro controller 102 can wirelessly receive the glucose data from a glucose monitoring unit using the wireless communication unit 108. In Step S2414, a glucose chart is displayed on the display unit based on the glucose data. For example, a glucose chart is displayed on the color LCD touch screen 106 based on the glucose data.

In Step S2416, blood pressure data is wirelessly received. For example, the micro controller 102 can wirelessly receive blood pressure data from a blood pressure monitoring unit using the wireless communication unit 108. In Step S2418, a blood pressure chart can be displayed on the display unit. For example, the micro controller 102 can display the blood pressure chart on the color LCD touch screen 106 using the blood pressure data.

In Step S2420, patient data can be received. For example, the micro controller can wirelessly receive the patient data from a computer and/or a medical device using the wireless communication unit 108. In Step S2422, the patient data can be displayed. For example, the micro controller 102 can display the patient data on the color LCD touch screen 106.

In Step S2424, gastric band implantation data can be received. For example, the micro controller 102 can wirelessly receive the gastric band implantation data from a computer and/or a medical device using the wireless communication unit 108. In Step S2426, the gastric band implantation data can be displayed on a display unit. For example, the micro controller 102 can display the gastric band implantation data on the color LCD touch screen 106. In Step S2428, the medical data can be transferred and received from a computer. For example, the micro controller 102 can transfer and receive the medical data from a computer.

In one embodiment, any transfer of data between the band information system 100 and a computer and/or a medical device can be encrypted. Furthermore any medical data and/or patient data can be stored in the flash memory 104. The medical data and/or the patient data can be further analyzed and/or used to create various charts, including charts using one or more types of medical data and/or patient data.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A portable gastric band information system for determining an adjustment amount to a gastric band implanted in a patient, comprising:
    a memory unit;
    a display unit; and
    a micro controller connected to the memory unit and the display unit, the micro controller configured to:
        use gastric band pressure data for the gastric band,
        receive weight loss data for the patient,
        receive satiety state data from the patient,
        receive a postoperative office visit sequence number, and
        determine which one algorithm of at least a plurality of different algorithms for the adjustment of the gastric band should be used to adjust the gastric band based on the postoperative office visit sequence number received,
        select the determined algorithm, and
        based on the selected algorithm, the micro controller is configured to determine an adjustment of the gastric band for the patient by analyzing the satiety state data of the patient and the weight loss data of the patient, and
        transmit the determined adjustment to a controller for the gastric band.

2. The system of claim 1 wherein the micro controller is further configured to receive glucose data, and display a glucose chart on the display unit based on the glucose data.

3. The system of claim 2 wherein the micro controller receives the glucose data from a glucose monitoring unit.

4. The system of claim 1 wherein the micro controller is further configured to receive blood pressure data, and display a blood pressure chart on the display unit based on the blood pressure data.

5. The system of claim 4 wherein the micro controller receives the blood pressure data from a blood pressure monitoring unit.

6. The system of claim 1 wherein the gastric band pressure data is realtime data.

7. The system of claim 1 wherein the micro controller receives the gastric band pressure data from a gastric band pressure monitoring unit, and the micro controller receives the weight data from a weight monitoring unit.

8. The system of claim 1 further comprising a wireless connection unit connected to the micro controller.

9. The system of claim 8 wherein the micro controller receives the gastric band pressure data wirelessly from a gastric band pressure monitoring unit, and the micro controller receives the weight data wirelessly from a weight monitoring unit.

10. The system of claim 8 wherein the micro controller is configured to wirelessly transfer and receive medical data from a computer.

11. The system of claim 1 wherein the micro controller is configured to receive patient data, and display the patient data.

12. The system of claim 1 wherein the micro controller is configured to receive gastric band implantation data, and display the gastric band implantation data.

13. The system of claim 1, wherein the micro controller is configured to wirelessly transmit the determined adjustment.

14. The system of claim 13, wherein the controller controls tightening and loosening of the gastric band.

15. The system of claim 13, wherein the controller controls a syringe in fluid communication with the gastric band.

16. The system of claim 1, wherein the controller controls tightening and loosening of the gastric band.

17. The system of claim 1, wherein the controller controls a syringe in fluid communication with the gastric band.

18. The system of claim 1, wherein the micro controller is configured to display a gastric band pressure chart on the display unit based on the gastric band pressure data.

19. The system of claim 1, wherein the micro controller is configured to display a weight chart on the display unit based on the weight data.

20. The system of claim 18, wherein the micro controller is configured to display a weight chart on the display unit based on the weight data.

* * * * *